United States Patent
Ellis et al.

(10) Patent No.: US 6,432,420 B2
(45) Date of Patent: *Aug. 13, 2002

(54) HAIR TREATMENT COMPOSITIONS

(75) Inventors: Frances Ellis, Bebington (GB); Takahiro Hiraishi; Tadashi Numata, both of Tochigi (JP); Matthew Pearce, Bebington (GB)

(73) Assignee: Unilever Home & Personal Care USA division of Conopco, Inc., Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/321,009

(22) Filed: May 27, 1999

(30) Foreign Application Priority Data

Jun. 1, 1998 (GB) ............................................. 9811754

(51) Int. Cl.$^7$ ........................... A61K 7/00; A61K 9/127
(52) U.S. Cl. ...................... 424/401; 424/450; 424/70.1; 424/70.11; 424/70.12; 514/880; 514/881
(58) Field of Search ................................. 424/401, 450, 424/70.11, 70.12, 70.1; 514/880, 881

(56) References Cited

U.S. PATENT DOCUMENTS

| 4,942,038 A | * | 7/1990 | Wallach | ...................... 424/450 |
| 5,246,693 A | | 9/1993 | Grollier et al. | |
| 5,429,820 A | * | 7/1995 | Kamitani | ...................... 424/401 |
| 5,641,508 A | * | 6/1997 | Li | ............................... 424/450 |

FOREIGN PATENT DOCUMENTS

| FR | 1603765 | 7/1971 |
| GB | 2004741 | 4/1979 |
| WO | 94/09750 | 11/1994 |
| WO | 95/22311 | 8/1995 |

OTHER PUBLICATIONS

Search Report under Section 17 Application No. GB 98/11754.2 dated Aug. 24, 1998.
Abstract of SU 1,528,494 A assigned to Biochem. Inst. Feb. 1987.
Abstract of JP 10,001,423 A assigned to Kanebo Ltd. Jan. 1998.
Abstract of FR 1,603,765 A assigned to Leclercq & P. Lechat, May 1971.
AN 90–296104 & SU 1528494 (12/89) assigned to Biochem Inst. (English language Derwent Abstract).

* cited by examiner

Primary Examiner—Gollamudi S. Kishore
(74) Attorney, Agent, or Firm—Matthew Boxer

(57) ABSTRACT

The invention provides a hair treatment composition such as a shampoo or conditioner suitable for topical application to hair for the repair and prevention of damage, comprising (i) cholesterol, and (ii) a hair benefit agent which is a mixture of a basic amino acid and a fatty acid. Preferably the cholesterol and hair benefit agent are compounded into a dispersion of multilamellar vesicles, stabilised with nonionic surfactant.

2 Claims, No Drawings

HAIR TREATMENT COMPOSITIONS

FIELD OF THE INVENTION

The invention relates to hair treatment compositions. More particularly the invention relates to hair treatment compositions comprising cholesterol in combination with certain hair benefit agents, which compositions are particularly suitable for application to hair for repair and restoration of damaged hair, and for moisturisation and protection of the hair fibre against future damage.

BACKGROUND AND PRIOR ART

Hair can suffer damage from a number of sources. The hair fibre can be damaged by environmental influences such as exposure to UV and chlorine; chemical influences such as bleaching, perming, overfrequent washing with harsh surfactant based cleansing shampoo compositions; and mechanical influences such as prolonged use of heated styling appliances.

Damage to the hair typically manifests itself in cuticle and protein loss from the hair fibre, excessive fibre stiffness, hair fibre brittleness and breakage and frayed or split ends.

A wide array of ingredients are claimed to be effective in the treatment and prevention of hair damage, as can be seen from the literature and from marketed products.

For example, certain amino acids are known to provide beneficial results in the prevention and treatment of hair damage. A number of shampoo and conditioner formulations are on the market which contain aloe vera extract, a substance rich in arginine, as an ingredient for fibre repair and moisturisation. Literature references include DE 3118882-A, which describes a tonic for hair which contains a mixture of amino acids. In this mixture, a 1:4:12 histidine:lysine:arginine ratio is said to stimulate keratin formation. FR 2669224-A describes a scalp treatment comprising aminodicarboxylic acid complexed with a basic amino acid complex as the active ingredient. The complex is said to prevent degradation of the hair root and improve the hydration of the hair keratin by neutralisation of scalp lactic acid. U.S. Pat. No. 4,201,235 describes hair treatment with a "cocktail" of 20 different amino acids and vitamins to enhance softness, lustre and body.

WO93/15709 is directed to the treatment and prevention of damage to keratinous material. This document describes a composition comprising an "oleophilic liquid vehicle" which is preferably a mixture of oleic, palmitic and linoleic acids, for infusing the other reagents in the composition into the hair shaft. The other reagents are a higher n-alkane such as eicosane, which is said to bond hydrophobically to keratin, and preferably a long chain dibasic acid such as sebacic acid, which is postulated to cross-link and therefore reinforce keratin chains at damage sites.

There remains a need for topical hair treatment compositions which deliver improved damage repair and protection to the hair.

The present inventors have now found that the penetration of certain hair benefit agents into the hair fibre from a topical hair treatment product can be specifically enhanced by the inclusion of cholesterol in the hair treatment composition. Compositions according to the present invention demonstrate improved efficacy in the repair and prevention of the principal symptoms of damaged hair.

SUMMARY OF THE INVENTION

In a first aspect, the present invention provides a hair treatment composition suitable for topical application to hair for the repair and prevention of damage, comprising:

(i) cholesterol, and
(ii) a hair benefit agent which is a mixture of a basic amino acid and a fatty acid.

DETAILED DESCRIPTION AND PREFERRED EMBODIMENTS

Cholesterol

Cholesterol is an essential component of the compositions of this invention.

The level of cholesterol in the composition is suitably from 0.005 to 0.1%, preferably from 0.01 to 0.05%, optimally from 0.02 to 0.03%, by weight based on the total weight of the composition.

Hair Benefit Agent

Compositions of the invention contain as a further essential component, a hair benefit agent which is a mixture of a basic amino acid and a fatty acid.

Basic Amino Acids

By "basic amino acid" is meant those amino acids having more basic groups than carboxyl groups. Suitable basic amino acids are L-arginine, DL-arginine hydrochloride, L-histidine, DL-histidine, L-lysine, and DL-lysine. L-Arginine is particularly preferred.

Simple derivatives of the basic amino acid may also be employed, such as salts and hydrosalts.

A particularly preferred example of a hydrosalt is a hydrohalide, especially the hydrochloride derivative.

It is further possible to employ other derivatives such as acyl, ester and peptide derivatives. These too may be used as salts or hydrosalts.

Examples are N-alkanoyl derivatives in which the alkanoyl moiety has an alkyl chain length of from 3 to 20 carbon atoms, preferably from 4 to 10 carbon atoms, e.g. N-butanoyl, N-hexanoyl and N-octanoyl, N-alkyl or COO-alkyl derivatives in which the alkyl group is straight chain and from 1 to 20 carbon atoms, preferably from 1 to 4 carbon atoms, e.g. methyl, ethyl and n-propyl and peptide derivatives in which the peptide residue comprises from 2 to 8 amino acid residues or substituted amino acid residues.

The level of basic amino acid in the composition is suitably from 0.005 to 0.5%, preferably from 0.01 to 0.4%, optimally from 0.1 to 0.3%, by weight based on the total weight of the composition.

Fatty Acids

By "fatty acid" is meant those compounds represented by the general formula RCOOH, wherein R denotes a saturated or unsaturated hydrocarbon radical having from 7 to 25, preferably from 10 to 22 carbon atoms on average—the hydrocarbon radical having a straight or branched chain or having hydroxyl group.

Suitable fatty acids are branched chain fatty acids such as 18-methyleicosanoic acid and other homologues of this series, straight chain fatty acids such as stearic, myristic and palmitic acids, and unsaturated fatty acids such as oleic acid, linoleic acid, linolenic acid and arachidonic acid. The fatty acids may be added singly, as mixtures, or in the form of blends derived from extracts of, e.g. lanolin. Oleic acid is a particularly preferred fatty acid, since this is a principal component of the natural free fatty acid content of hair.

The level of fatty acid in the composition is suitably from 0.005 to 0.1%, preferably from 0.01 to 0.05%, optimally from 0.02 to 0.03%, by weight based on the total weight of the composition.

A particularly preferred combination is L-arginine and oleic acid.

The total weight of hair benefit agent in compositions of the invention is suitably from 0.005% to 5%, preferably from 0.085% to 2%, most preferably from 0.1 to 0.5% by total weight of hair benefit agent based on the total weight of the hair treatment composition.

Preparation Process

Advantageously, in hair treatment compositions of the invention, the cholesterol and hair benefit agent may be compounded into a dispersion of multilamellar vesicles. This is highly preferred, since it is a convenient way of enhancing the efficacy of hair treatment compositions of the invention in the repair and prevention of the principal symptoms of damaged hair.

Thus, in a further aspect the present invention provides a hair treatment composition comprising a dispersion of multilamellar vesicles, the vesicles being formed of cholesterol, basic amino acid and fatty acid.

The dispersion of multilamellar vesicles may conveniently be prepared by the following steps:

(i) compounding the fatty acid with the cholesterol, and
(ii) adding the mixture so obtained to an aqueous solution of the basic amino acid.

In step (i), preferred fatty acids are as described above under the heading "Fatty Acids". Especially preferred is oleic acid.

In general, if the amount of fatty acid relative to the amount of cholesterol is too low, then difficulties in compounding may be encountered. Conversely, too high an amount of fatty acid may be detrimental to conditioning performance of the final product. A suitable weight ratio of cholesterol to fatty acid (e.g. oleic acid) in step (i) was found to be about 3:1 to 1:2. Optimally, the weight ratio was found to be about 1:1, in terms of ease of processing, stability of the multilamellar vesicles and product performance.

In step (ii), in order to disperse the mixture of cholesterol and free fatty acid successfully, a basic (alkaline) aqueous solution was found to be an essential requirement. For example, aqueous solutions of derivatives of basic amino acids which are in salt form and therefore neutral (e.g. L-arginine monohydrochloride) are not suitable in this method, whereas aqueous solutions of free basic amino acid (e.g. L-arginine), are suitable.

The above process gives rise to the formation of a dispersion of multilamellar vesicles, which can be observed by polarised optical microscopy.

It is highly preferred to add a nonionic surfactant to the above dispersion. This has been found to improve the stability of the multilamellar vesicles towards the type of pH value normally encountered in hair treatment compositions (e.g. 6–7).

Suitable nonionic surfactants include condensation products of aliphatic ($C_8$–$C_{18}$) primary or secondary linear or branched chain alcohols or phenols with alkylene oxides, usually ethylene oxide and generally having from 4 to 30 ethylene oxide groups. Preferred nonionic surfactants are polyoxyethylene alkyl ethers and polyoxyethylene alkyl esters. Examples are polyoxyethylene lauric, myristic, and cetyl ethers, and sorbitan fatty acid esters such as Polysorbate 20 and Polysorbate 80.

After addition of nonionic surfactant as described above, it is preferred to adjust the pH of the dispersion of multilamellar vesicles to around 6–7, before blending with the remaining formulation ingredients to form the final hair treatment composition. This may typically be accomplished by addition of a suitable acid, e.g. an organic acid such as lactic acid, acetic acid, citric acid, or an inorganic mineral acid such as hydrochloric acid.

Advantages of the above process include the fact that dispersion of cholesterol and fatty acid may be effected by simple stirring (no special equipment or mixing facilities required) and the short processing time (generally no longer than about 40 minutes).

Product Form

The final product form of hair treatment compositions according to the invention may suitably be, for example, shampoos, conditioners, sprays, mousses or lotions. Particularly preferred product forms are shampoos, post-wash conditioners (leave-in and rinse-off) and hair treatment products such as hair essences.

Shampoo Compositions

A particularly preferred hair treatment composition in accordance with the invention is a shampoo composition.

Cleansing Surfactant

Such a shampoo composition will comprise one or more cleansing surfactants which are cosmetically acceptable and suitable for topical application to the hair. Further surfactants may be present as an additional ingredient if sufficient for cleansing purposes is not provided as emulsifying agent for oily or hydrophobic components (such as silicones) which may typically be present in the shampoo.

It is preferred that shampoo compositions of the invention comprise at least one further surfactant (in addition to that used as emulsifying agent) to provide a cleansing benefit.

Suitable cleansing surfactants, which may be used singularly or in combination, are selected from anionic, amphoteric and zwitterionic surfactants, and mixtures thereof. The cleansing surfactant may be the same surfactant as the emulsifier, or may be different.

Examples of anionic surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic surfactants for use in shampoos of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, triethanolamine monolauryl phosphate, sodium lauryl ether sulphate 1 EO, 2EO and 3EO, ammonium lauryl sulphate and ammonium lauryl ether sulphate 1EO, 2EO and 3EO.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

The shampoo composition can also include co-surfactants, to help impart aesthetic, physical or cleansing properties to the composition. A preferred example is a nonionic surfactant, which can be included in an amount ranging from 0% to about 5% by weight based on total weight.

For example, representative nonionic surfactants that can be included in shampoo compositions of the invention include condensation products of aliphatic ($C_8$–$C_{18}$) primary or secondary linear or branched chain alcohols or phenols with alkylene oxides, usually ethylene oxide and generally having from 6 to 30 ethylene oxide groups.

Other representative nonionics include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

$$RO-(G)_n$$

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

The total amount of surfactant (including any co-surfactant, and/or any emulsifying agent) in shampoo compositions of the invention is generally from 0.1 to 50% by weight, preferably from 5 to 30%, more preferably from 10% to 25% by weight of the total shampoo composition.

Cationic Polymer

A cationic polymer is a preferred ingredient in shampoo compositions of the invention, for enhancing conditioning performance of the shampoo. Typically such a polymer enhances deposition of conditioning components such as silicone from the shampoo composition onto the intended site during use, i.e. the hair and/or the scalp.

The cationic polymer may be a homopolymer or be formed from two or more types of monomers. The molecular weight of the polymer will generally be between 5 000 and 10 000 000, typically at least 10 000 and preferably in the range 100 000 to about 2 000 000. The polymers will have cationic nitrogen containing groups such as quaternary ammonium or protonated amino groups, or a mixture thereof.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic polymers can comprise mixtures of monomer units derived from amine- and/or quaternary ammonium-substituted monomer and/or compatible spacer monomers.

Suitable cationic polymers include, for example:
copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);

copolymers of 1-vinyl-2-pyrrolidine and dimethylaminoethyl methacrylate, referred to in the industry (CTFA) as Polyquaternium-11. This material is available commercially from Gaf Corporation (Wayne, N.J. USA) under the GAFQUAT tradename (e.g., GAFQUAT 755N);

cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo-and co-polymers of unsaturated carboxylic acids having from 3 to 5 carbon atoms, (as described in U.S. Pat. No. 4,009,256);

cationic polyacrylamides (as described in WO95/22311).

Other cationic polymers that can be used include cationic polysaccharide polymers, such as cationic cellulose derivatives, cationic starch derivatives, and cationic guar gum derivatives.

Cationic polysaccharide polymers suitable for use in compositions of the invention include those of the formula:

$$A-O-[R-N^+(R^1)(R^2)(R^3)X^-],$$

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J. USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (Commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic polymer is selected from cationic cellulose and cationic guar derivatives. Particularly preferred cationic polymers are JAGUAR C13S, JAGUAR C15, JAGUAR C17 and JAGUAR C16 and JAGUAR C162.

Conditioners

Conditioning Surfactant

Compositions in accordance with the invention may also be formulated as conditioners for the treatment of hair (typically after shampooing) and subsequent rinsing. Such a conditioner will comprise one or more conditioning surfactants which are cosmetically acceptable and suitable for topical application to the hair.

Suitable conditioning surfactants are selected from cationic surfactants, used singly or in admixture.

Examples of suitable cationic conditioning surfactants include quaternary ammonium cationic surfactants.

Suitable quaternary ammonium cationic surfactants for use in hair conditioners of the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further suitable cationic surfactants include those materials having the CTFA designations Quaternium-5, Quaternium-31 and Quaternium-18.

Mixtures of any of the foregoing materials may also be suitable. A particularly useful cationic surfactant for use in hair conditioners of the invention is cetyltrimethylammonium chloride, available commercially, for example as GENAMIN CTAC, ex Hoechst Celanese.

A further preferred class of cationic conditioning surfactants are acid-neutralised amidoamine compounds of the general structural formula (I):

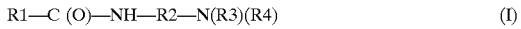

R1—C (O)—NH—R2—N(R3)(R4)     (I)

wherein R1 is a fatty acid chain containing from 12 to 22 carbon atoms, R2 is an alkylene group containing from one to four carbon atoms, and R3 and R4 are, independently, an alkyl group having from one to four carbon atoms.

Examples of suitable amidoamine compounds of general structural formula (I) include stearamidopropyl dimethylamine, stearamidopropyl diethylamine, stearamidoethyl dimethylamine, stearamidoethyl diethylamine, palmitamidopropyl dimethylamine, behenamidopropyl dimethylamine, myristamidopropyl dimethylamine, oleamidopropyl dimethylamine, ricinoleamidopropyl dimethylamine, and combinations thereof.

The acid used to neutralise the amidoamine compound can be essentially any organic acid or mineral acid of sufficient acid strength to neutralise a free amine nitrogen. Such acids include hydrochloric acid, sulphuric acid, nitric acid, phosphoric acid, lactic acid, citric acid, tartaric acid, acetic acid, gluconic acid, glycolic acid and propionic acid, or combinations thereof. A preferred acid is lactic acid, since neutralisation of the amidoamine compound with this acid yields an exceptionally stable composition.

In general, a sufficient amount of acid is added to neutralise the amidoamine compound and to adjust the final pH of the composition to within a range of from about 2.5 to about 6, preferably in a pH range of from about 3 to about 5.

In conditioners of the invention, the level of cationic surfactant is preferably from 0.01 to 10%, more preferably 0.05 to 5%, most preferably 0.1 to 2% by total weight of cationic surfactant based on the total weight of the composition.

Fatty Alcohol

Conditioners of the invention advantageously incorporate a fatty alcohol. The combined use of fatty alcohols and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 20. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol in conditioners of the invention is conveniently from 0.01 to 10%, preferably from 0.1 to 5% by weight of the composition. The weight ratio of cationic surfactant to fatty alcohol is suitably from 10:1 to 1:10, preferably from 4:1 to 1:8, optimally from 1:1 to 1:4.

Silicone

Silicone is a particularly preferred ingredient in hair treatment compositions of the invention. In particular, hair shampoos and conditioners of the invention will preferably also comprise emulsified particles of silicone, for enhancing conditioning performance. The silicone is insoluble in the aqueous matrix of the composition and so is present in an emulsified form, with the silicone present as dispersed particles.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol, and polydimethylsiloxanes having containing at least one amino functional group, which have the CTFA designation amodimethicone or trimethylsilylamodimethicone.

Examples of suitable materials include:
the DC200 series of silicone fluids, available from Dow Corning (e.g. DC200, viscosity 350 cs), or SF96 or the VISCASIL series of silicones, available from General Electric Silicones;
silicone gums such as SE30, SE54 and SE76, available from General Electric Silicones;
silicone gum/fluid blends such as Q2-1403 available from Dow Corning, or CF 1251, available from General Electric Silicones;
pre-formed emulsions of dimethiconol such as emulsions DC2-1766, DC2-1784, and microemulsions DC2-1865 and DC2-1870, all available from Dow Corning;
amino functional silicones such as Q2-8220 and Q2-8466 fluids, available from Dow Corning, and also SF-1708-D1, available from General Electric Silicones;
pre-formed emulsions of amino functional silicones such as DC929 Cationic Emulsion, DC939 Cationic Emulsion, and the non-ionic emulsions DC2-7224, DC2-8467, DC2-8177 and DC2-8154 (all ex Dow Corning);
silicone gum/silicone fluid/amino functional silicone blends.

Most preferably, the silicone for inclusion in the hair treatment composition of the invention, is sourced as a pre-formed aqueous emulsion, for example a mechanically-formed aqueous emulsion. In such emulsions, it is highly preferable that the emulsion additionally includes at least one emulsifier in order to stabilise the silicone emulsion. Suitable emulsifiers are well known in the art and include anionic and nonionic surfactants.

Preferably, the average particle size of the silicone droplets in the emulsion and also in the final hair treatment composition is less than 20 microns, more preferably less than 10 microns. A smaller silicone particle size enables a more uniform distribution of silicone on the hair for the same amount of silicone in the composition.

A particularly suitable silicone emulsion for use in compositions of the invention is an emulsion containing silicone gum with a viscosity greater than 1 Mcs, silicone fluid with a viscosity of less than 100 kcs and an amino functional silicone, in a nonionic surfactant base, of silicone particle size 5 microns.

Silicone particle size in the emulsion may be measured by means of a laser light scattering technique, for example using a 2600D Particle Sizer from Malvern Instruments.

Viscosity (of the silicone itself and not the emulsion or the final hair treatment composition) can be measured by means of a glass capillary viscometer as set out further in Dow Corning Corporate Test Method CTM004, Jul. 20, 1970.

The total amount of silicone incorporated into hair treatment compositions of the invention depends on the level of conditioning desired and the material used. A preferred amount is from 0.01 to about 10% by weight of the total composition although these limits are not absolute. The lower limit is determined by the minimum level to achieve conditioning and the upper limit by the maximum level to avoid making the hair and/or skin unacceptably greasy.

We have found that a total amount of silicone of from 0.3 to 5%, preferably 0.5 to 3%, by weight of the total composition is a suitable level.

Solvents and Carriers

Composition of the invention are preferably aqueous based, but non-aqueous solvents also can be used in order to help solubilise ingredients that are not sufficiently soluble in water. Suitable non-aqueous solvents include the lower alcohols like ethyl alcohol and propyl alcohol; polyols like glycerol; glycols or glycol ethers, like 2-butoxyethanol, ethylene glycol, ethylene glycol monoethyl ether, propylene glycol and diethylene glycol monoethyl ether or monomethyl ether and mixtures thereof. These non-aqueous solvents can be present in the composition of the invention in an amount of from 1 to 100%, preferably 5 to 50%, by weight based on the total weight of the vehicle of the composition of the invention.

Optional Ingredients

Compositions of this invention may contain any other ingredient normally used in hair treatment formulations. These other ingredients may include viscosity modifiers, preservatives, colouring agents, polyols such as glycerine and polypropylene glycol, chelating agents such as EDTA, antioxidants such as vitamin E acetate, fragrances, antimicrobials and sunscreens. Each of these ingredients will be present in an amount effective to accomplish its purpose. Generally these optional ingredients are included individually at a level of up to about 5% by weight of the total composition.

The invention is further illustrated by way of the following non-limitative examples. All percentages quoted are by weight based on total weight unless otherwise stated.

EXAMPLE 1

Preparation of a dispersion of multilamellar vesicles containing L-Arginine, Cholesterol and Oleic acid Step 1: Add L-Arginine to hot water at 80 degrees C.
Step 2: Mix Cholesterol and Oleic Acid in 1:1 ratio
Step 3: Add mixture of cholesterol and oleic acid to L-arginine solution and mix until dispersed completely (about 30 minutes.
(At this stage, multilamellar vesicles can be observed by polarised optical microscopy)
Step 4: Add 1:1 mixture of polyoxyethylene (4.2) lauryl ether and polyoxyethylene (25) lauryl ether to stabilise vesicles
Step 5: Adjust pH to 6–7 with citric acid

EXAMPLE 2

The dispersion obtained from Example 1 above may be blended with shampoo ingredients to form a shampoo composition having the following composition:

| Component | % by weight |
|---|---|
| Sodium lauryl ether sulphate 2EO (70% a. i.) | 9.02 |
| Pearlised sodium lauryl ether sulphate 2EO (13.8% a. i.) | 13.00 |
| Cocamidopropyl betaine (30% a. i.) | 13.34 |
| JAGUAR C13S | 0.30 |
| Dimethicone emulsion $10^6$ cs (60% a. i.) | 2.5 |
| Dimethicone emulsion $10^5$ cs (40% a. i.) | 3.75 |
| Oleic acid | 0.025 |
| L-Arginine | 0.2 |
| Cholesterol | 0.025 |
| Polyoxyethylene (4.2) lauryl ether | 0.0025 |
| Polyoxyethylene (25) lauryl ether | 0.0025 |
| Citric acid | 0.165 |
| Preservative, colour, fragrance | q.s. |
| Water, minors | to 100% |

The above shampoo is particularly effective when applied to hair for the repair and prevention of damage.

EXAMPLE 3

The dispersion obtained from Example 1 above may be blended with conditioner ingredients to form a conditioner having the following composition:

| Component | % by weight |
|---|---|
| Cetyl trimethylammonium chloride (25% a. i.) | 4.0 |
| Cetostearyl alcohol | 1.21 |
| Paraffin wax | 1.0 |
| Silicone emulsion[1] | 3.33 |
| Oleic acid | 0.025 |
| L-Arginine | 0.2 |
| Cholesterol | 0.025 |
| Polyoxyethylene (4.2) lauryl ether | 0.0025 |
| Polyoxyethylene (25) lauryl ether | 0.0025 |
| Citric acid | 0.072 |
| Hydroxyethylcellulose | 0.35 |
| Preservative, colour, fragrance | q.s. |
| Water, minors | to 100% |

[1]Added as 60% a. i. emulsion of 13 Mcs dimethicone gum, 200 cs dimethicone fluid and amino functional silicone, in a nonionic surfactant base, of silicone particle size 5 microns.

The above conditioner is particularly effective when applied to hair as a post-wash treatment for the repair and prevention of damage.

What is claimed is:

1. A hair damage repair and hair protection composition comprising a dispersion of multi-lamellar vesicles formed of cholesterol, a basic amino acid, and a fatty acid:

wherein:
   (1) cholesterol is present at 0.005% to 0.1%;
   (2) basic amino acid is present at 0.005% to 5%; and
   (3) fatty acid is present at 0.005% to 0.1%;
      and wherein the basic amino acid is selected from the group consisting of L-arginine, DL-arginine hydrochloride, L-histidine, L-lysine, and DL-lysine;
      and wherein the fatty acid is a compound of the formula RCOOH, wherein R is a saturated or unsaturated hydrocarbon radical having from 7 to 25 carbon atoms;
      and wherein the ratio of said cholesterol to said fatty acid, at the time said cholesterol and said fatty acid are compounded, is about 3:1 to 1:2.

2. A hair damage repair and hair protection composition comprising a dispersion of multi-lamellar vesicles consisting of cholesterol, a basic amino acid, and a fatty acid:

wherein:
   (1) cholesterol is present at 0.005% to 0.1%;
   (2) basic amino acid is present at 0.005% to 5%; and
   (3) fatty acid is present at 0.005% to 0.1%;
      and wherein the basic amino acid is selected from the group consisting of L-arginine, DL-arginine hydrochloride, L-histidine, L-lysine, and DL-lysine;
      and wherein the fatty acid is a compound of the formula RCOOH, wherein R is a saturated or unsaturated hydrocarbon radical having from 7 to 25 carbon atoms;
      and wherein the ratio of said cholesterol to said fatty acid, at the time said cholesterol and said fatty acid are compounded, is about 3:1 to 1:2.

\* \* \* \* \*